United States Patent [19]

Jørgensen et al.

[11] Patent Number: 6,048,856
[45] Date of Patent: Apr. 11, 2000

[54] HETEROCYCLIC COMPOUNDS

[75] Inventors: Tine Krogh Jørgensen, Ølstykke; Erik Fischer, Charlottenlund; Rolf Hohlweg, Kvistgaard; Knud Erik Andersen, Smørum; Uffe Bang Olsen, Vallensbæk, all of Denmark; Karel Sindelar, Prague, Czechoslovakia; Alexandra Silhankova, Prague, Czechoslovakia; Otylie Konigova, Prague, Czechoslovakia; Zdeněk Polivka, Prague, Czechoslovakia

[73] Assignee: Novo Nordisk A/S, Bagsvaerd, Denmark

[21] Appl. No.: 09/211,378

[22] Filed: Dec. 14, 1998

Related U.S. Application Data

[60] Provisional application No. 60/082,049, Dec. 18, 1997.

[30] Foreign Application Priority Data

Dec. 17, 1997 [DK] Denmark .................................. 1472/97

[51] Int. Cl.⁷ ........................ A61K 31/55; A61K 31/435; C07D 211/06; C07D 223/18
[52] U.S. Cl. .......................... 514/217; 546/203; 540/587; 514/325
[58] Field of Search ...................... 540/484, 587; 514/215, 317, 325, 217; 546/195, 203

[56] References Cited

U.S. PATENT DOCUMENTS

| | | | |
|---|---|---|---|
| 3,063,996 | 11/1962 | Gorden | 544/42 |
| 3,481,930 | 12/1969 | Childress et al. | 540/596 |

FOREIGN PATENT DOCUMENTS

| | | |
|---|---|---|
| 0 293 813 | 12/1988 | European Pat. Off. . |
| 25 02 326 | 7/1975 | Germany . |
| 1 228 736 | 4/1971 | United Kingdom . |
| 1 294 550 | 11/1972 | United Kingdom . |
| 1 330 966 | 9/1973 | United Kingdom . |
| WO 96/31498 | 10/1996 | WIPO . |

OTHER PUBLICATIONS

Chemical Abstract, vol. 66, No. 13, p. 5247 (Mar. 27, 1967).
Chemical Abstract, vol. 59, No. 8, abstract No. 8750 (Oct. 14, 1963).
Chemical Abstract, vol. 127, No. 19, p. 633 (Nov. 10, 1997) Miyamoto, et al.
Chemical Abstract, vol. 72, No. 1 p. 308 (Jan. 5, 1970).
Chemical Abstract, vol. 123, No. 23, p. 908 (Dec. 4, 1995).

*Primary Examiner*—Zinna Northington Davis
*Assistant Examiner*—Binta Robinson
*Attorney, Agent, or Firm*—Steve T. Zelson; Carol E. Rozek

[57] ABSTRACT

The present invention relates to novel N-substituted azaheterocyclic compounds of the formula

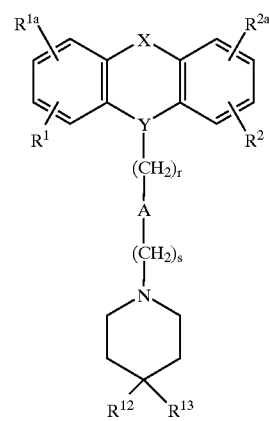

wherein X, Y, $R^1$, $R^{1a}$, $R^2$, $R^{2a}$, $R^{12}$, $R^{13}$, A, r and s are as defined in the detailed part of the present description, or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation. These compounds are also useful for treating indications caused by or related to the secretion and circulation of insulin antagonizing peptides, e.g., non-insulin-dependent diabetes mellitus (NIDDM) and ageing-associated obesity.

18 Claims, No Drawings

HETEROCYCLIC COMPOUNDS

CROSS-REFERENCE TO RELATED APPLICATIONS

This application claims priority under 35 U.S.C. 119 of U.S. provisional application No. 60/082,049 filed Dec. 18, 1997 and Danish application No. 1472/97 filed Dec. 17, 1997, the contents of which are fully incorporated herein by reference.

FIELD OF INVENTION

The present invention relates to novel N-substituted azaheterocyclic compounds in which a substituted alkyl chain forms part of the N-substituent or salts thereof, to methods for their preparation, to compositions containing them, to the use of the compounds for preparing compositions for the clinical treatment of painful, hyperalgesic and/or inflammatory conditions in which C-fibres play a pathophysiological role, and to methods of treating said painful, hyperalgesic and/or inflammatory conditions. The invention also relates to the use of the present compounds for reducing blood glucose and/or inhibit the secretion, circulation or effect of insulin antagonizing peptides like CGRP or amylin, the present compounds being known to iterfere with neuropeptide containing C-fibres. Hence the present compounds can be used in the treatment of non-insulin-dependent diabetes mellitus (NIDDM) in order to improve the glucose tolerance as well as ageing-associated obesity.

BACKGROUND OF INVENTION

The nervous system exerts a profound effect on the inflammatory response. Antidromic stimulation of sensory nerves results in localised vasodilation and increased vascular permeability (Janecso et al. Br. J. Pharmacol. 1967, 31, 138–151), and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity may be useful in treatment of for example arthritis, dermatitis, rhinitis, asthma, cystitis, gingivitis, thrombophlelitis, glaucoma, gastro-intestinal diseases or migraine.

Furthermore, the fact that the C-fibers innervate the liver, the intestines and the pancreas suggests that they control various function. The peptidergic innervation has been shown to control glucose tolerance in rodents (Karlsson et al. Am. J. Physiol. 267, R1071–R1077, 1994, Guillot et al. Life Sci. 969–977, 1996).

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or ageing-associated obesity (Melnyk et al. Obesity Res. 3, 337–344, 1995) where circulating plasma levels of CGRP are markedly increased. Hence inhibition of release and/or activity of the neuropeptide CGRP and other sensory neuropeptides may be useful in the treatment of insulin resistance related to type 2 diabetes or ageing.

In U.S. Pat. Nos. 4,383,999 and 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. In GB 1228736, GB 1294550 and GB 1330966 derivatives of N-substituted piperidines are claimed as being useful as psychotropic agents. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake. WO 9631498 discloses N-substituted azaheterocyclic carboxylic acids and esters thereof.

SUMMARY OF THE INVENTION

The present invention relates to compounds of the general formula I, wherein X, Y, $R^1$, $R^{1a}$, $R^2$, $R^{2a}$, $R^{12}$, $R^{13}$, A, r and s are as defined in the detailed part of the present description.

The present compounds are useful for the treatment, prevention, elimination, alleviation or amelioration of an indication related to all painful, hyperalgesic and/or inflammatory conditions in which C-fibres play a pathophysiological role, e.g. neurogenic pain, neurogenic inflammation, migraine, neuropathy, itching and rheumatoid arthritis, as well as indications caused by or related to the secretion and circulation of insulin antagonising peptides and other peptides derived from the sensory nervous system, e.g. non-insulin-dependent diabetes mellitus (NIDDM) and ageing-associated obesity.

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

In another aspect of the present invention there is provided a method of treating painful, hyperalgesic and/or inflammatory conditions in which C-fibres play a pathophysiological role, e.g. neurogenic pain, neurogenic inflammation, migraine, neuropathy, itching and rheumatoid arthritis, as well as a method of treating indications caused by or related to the secretion and circulation of insulin antagonising peptides, e.g. non-insulin-dependent diabetes mellitus (NIDDM) and ageing-associated obesity.

The method of treatment may be described as the treatment, prevention, elimination, alleviation or amelioration of one of the above indications, which comprises the step of administering to the said subject a neurologically effective amount of a compound of the invention, or a pharmaceutically acceptable salt thereof.

A further aspect of the invention relates to the use of a compound of the present invention for the preparation of a pharmaceutical composition for the treatment of all painful, hyperalgesic and/or inflammatory conditions in which C-fibres play a pathophysiological role, e.g. neurogenic pain, neurogenic inflammation, migraine, neuropathy, itching and rheumatoid arthritis, as well as for the treatment of indications caused by or related to the secretion and circulation of insulin antagonising peptides and other peptides derived from the sensory nervous system, e.g. non-insulin-dependent diabetes mellitus (NIDDM) and ageing-associated obesity.

Further objects will become apparent from the following description.

DETAILED DESCRIPTION OF THE INVENTION

Accordingly, the present invention relates to novel N-substituted azaheterocyclic compounds of the general formula I

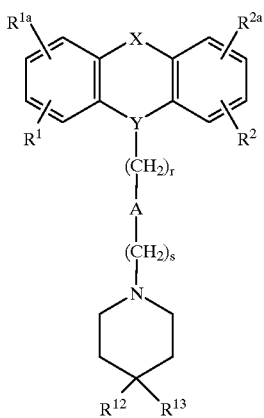

wherein $R^1$, $R^{1a}$, $R^2$ and $R^{2a}$ independently are hydrogen, halogen, cyano, trifluoromethyl, methylthio, hydroxy, $C_{1-6}$-alkyl or $C_{1-6}$-alkoxy;

X is ortho-phenylene, —O—, —S—, —C($R^3R^4$)—, —CH$_2$CH$_2$—, —CH=CH—CH$_2$—, —CH$_2$—CH=CH—, —CH$_2$—(C=O)—, —(C=O)—CH$_2$—, —CH$_2$CH$_2$CH$_2$—, —CH=CH—, —N($R^5$)—(C=O)—, —(C=O)—N($R^5$)—, —O—CH$_2$—, —CH$_2$—O—, —O—CH$_2$—O—, —CH$_2$—O—CH$_2$—, —S—CH$_2$—, —CH$_2$—S—, —(CH$_2$)N($R^5$)—, —N($R^5$)(CH$_2$)—, —N(CH$_3$)SO$_2$—, —SO$_2$N(CH$_3$)—, —CH($R^6$)CH$_2$—, —CH$_2$CH($R^6$)—, —(C=O)—, —N($R^7$)— or —(S=O)— wherein $R^3$, $R^4$, $R^5$ and $R^7$ independently are hydrogen or $C_{1-6}$-alkyl and wherein $R^6$ is $C_{1-6}$-alkyl or phenyl;

Y is >N—, >CH—, >N—(C=O)— or >C=C($R^8$)— wherein only the underscored atom participates in the ring system and wherein $R^8$ is hydrogen or $C_{1-6}$-alkyl;

A is —CH=C$R^9$—, —C$R^9$=CH—, —C≡C—, —(C=O)—, —(C=CH$_2$)—, —(C$R^9R^{10}$)—, —CH(O$R^{11}$)—, —CH(NH$R^{11}$)—, phenylene, $C_{3-7}$-cycloalkylene or the completion of a bond wherein $R^9$ and $R^{10}$ independently are hydrogen, $C_{1-6}$-unbranched alkyl, $C_{3-6}$-branched alkyl or $C_{3-8}$-cycloalkyl and wherein $R^{11}$ is hydrogen or $C_{1-6}$ alkyl;

r and s independently are 0,1, 2, 3 or 4;

$R^{12}$ is hydrogen, —(CH$_2$)$_n$OH or —(CH$_2$)$_p$CO$R^{17}$ wherein n is 1, 2, 3, 4, 5 or 6 and wherein p is 0 or 1 and wherein $R^{17}$ is —OH, —NH$R^{20}$ or $C_{1-6}$-alkoxy wherein $R^{20}$ is hydrogen or $C_{1-6}$-alkyl; and $R^{13}$ is cyano, —N$R^5R^7$, —N$R^5$—Z or —(CH$R^{21}$)$_q$—Z wherein $R^5$ and $R^7$ are as defined above and wherein q is 0, 1, 2, 3, 4, 5 or 6, and wherein $R^{21}$ is hydrogen, halogen, cyano, trifluoromethyl, hydroxy, $C_{1-6}$-alkyl, $C_{1-6}$-alkoxy, —N$R^5R^7$ or —COOH, and wherein Z is $C_{3-8}$-cycloalkyl, aryl or heteroaryl, which rings may optionally be substituted with one or more of halogen, cyano, trifluoromethyl, hydroxy, methylthio, $C_{1-6}$-alkyl or $C_{1-6}$-alkoxy; or a pharmaceutically acceptable salt thereof.

Compounds of formula I wherein X is —S—and Y is >N—, >CH— or >C=CH—; or wherein X is —CH$_2$CH$_2$—, Y is >N—, $R^{12}$ is —CONH$_2$ and $R^{13}$ is —N(CH$_3$)$_2$ or piperidino; or wherein X is —O—, —C(CH$_3$)$_2$, —CH$_2$CH$_2$—, —CH=CH—, —O—CH$_2$—, —CH$_2$—O—, —S—CH$_2$— or —CH$_2$—S—; Y is >C=CH—, $R^{12}$ is hydrogen, hydroxy —CONH$_2$ or —COOC$_2$H$_5$ and $R^{13}$ is —N(CH$_3$)$_2$, piperidino, morpholino or phenyl wherein phenyl may optionally be substituted with chlorine, methyl or trifluoromethyl, are known from the prior art.

The compounds of formula I may exist as geometric and optical isomers and all isomers, as separated, pure or partially purified stereoisomers or racemic mixtures thereof are included in the scope of the invention. Isomers may be separated by means of standard methods such as chromatographic techniques or fractional crystallisation of suitable salts.

Preferably, the compounds of formula I exist as the individual geometric or optical isomers.

The compounds according to the invention may optionally exist as pharmaceutically acceptable acid addition salts, metal salts or, optionally alkylated, ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts. Further examples of pharmaceutically acceptable inorganic or organic acid addition salts include the pharmaceutically acceptable salts listed in Journal of Pharmaceutical Science, 66, 2 (1977) which are known to the skilled artisan.

Also included are the hydrates of the above mentioned acid addition salts which the present compounds are able to form.

The acid addition salts may be obtained as the direct products of compound synthesis. In the alternative, the free base may be dissolved in a suitable solvent containing the appropriate acid, and the salt isolated by evaporating the solvent or by precipitation or crystallisation.

The compounds of formula I may be administered in a pharmaceutically acceptable acid addition salt form or where possible as a metal or a lower alkylammonium salt. Such salt forms exhibit approximately the same order of activity as the free base forms.

In the above structural formula and throughout the present specification, the following terms have the indicated meaning:

The terms "$C_{1-6}$-alkyl" as used herein, alone or in combination, refers to a straight or branched, saturated hydrocarbon chain having 1 to 6 carbon atoms. Examples of such groups include, but are not limited to, methyl, ethyl, n-propyl, iso-propyl, n-butyl, sec-butyl, iso-butyl, tert-butyl, n-pentyl, iso-pentyl, 2-methylbutyl, 3-methylbutyl, n-hexyl, iso-hexyl, 4-methylpentyl, neopentyl, 1,2-dimethylpropyl, 2,2-dimethylpropyl, 1,2,2-trimethylpropyl and the like.

The term "halogen" means fluorine, chlorine, bromine or iodine.

The term "$C_{1-6}$-alkoxy" as used herein, alone or in combination is intended to include those $C_{1-6}$-alkyl groups of the designated length in either a linear or branched or cyclic configuration linked thorugh an ether oxygen having its free valence bond from the ether oxygen. Examples of linear alkoxy groups are methoxy, ethoxy, propoxy, butoxy, pentoxy and hexoxy. Examples of branched alkoxy are isoprpoxy, sec-butoxy, tert-butoxy, isopentoxy and isohexoxy. Example of cyclic alkoxy are cyclopropyloxy, cyclobutyloxy, cyclopentyloxy and cyclohexyloxy.

The term "$C_{3-8}$-cycloalkyl" as used herein, represents a carbocyclic group having from 3 to 8 carbon atoms, e.g. cyclopropyl, cyclobutyl, cyclopentyl, cyclohexyl, cycloheptyl and cyclooctyl and the like.

The term "$C_{3-7}$-cycloalkylene" as used herein represents a bisubstituted carbocyclic group having from 3 to 7 carbon atoms e.g. cyclopropylene, cyclobutylene, cyclopentylene, cyclohexylene and cycloheptylene and the like.

The term "aryl" as used herein is intended to include carbocyclic aromatic ring systems such as phenyl, naphthyl (1-naphthyl or 2-naphthyl), anthracenyl (1-anthracenyl, 2-anthracenyl, 3-anthracenyl), phenanthrenyl, fluorenyl, indenyl and the like.

The term "heteroaryl" as used herein is intended to include heterocyclic aromatic ring systems containing one or more heteroatoms selected from nitrogen, oxygen and sulfur, such as furyl, thienyl, pyrrolyl, oxazolyl, thiazolyl, imidazolyl, isoxazolyl, isothiazolyl, triazolyl, pyranyl, pyridyl, pyridazinyl, pyrimidinyl, pyrazinyl, triazinyl, thiadiazinyl, indolyl, isoindolyl, benzofuryl, benzothienyl, indazolyl, benzimidazolyl, benzthiazolyl, purinyl, quinozolinyl, quinolinyl, isoquinolinyl, quinoxalinyl, naphthyridinyl, pteridinyl, carbazolyl, acridinyl and the like. Heteroaryl is also intended to include the partially or fully hydrogenated derivatives of the heterocyclic systems enumerated above. Non-limiting examples of such partially or fully hydrogenated derivatives are pyrrolinyl, pyrazolinyl, indolinyl, pyrrolidinyl, piperidinyl, piperazinyl, azepinyl, diazepinyl, morpholinyl, thiomorpholinyl, oxazolidinyl, oxazolinyl, oxazepinyl, aziridinyl and tetrahydrofuranyl.

In a preferred embodiment of the invention $R^1$, $R^{1a}$, $R^2$ and $R^{2a}$ are selected from hydrogen, halogen, trifluoromethyl or $C_{1-6}$-alkyl. Preferably $R^1$, $R^{1a}$, $R^2$ and $R^{2a}$ are hydrogen.

In a another preferred embodiment of the invention X is selected from —S—, —$CH_2CH_2$—, —CH=CH—, —O—$CH_2$—, —$CH_2$—O—, —$OCH_2O$—, —S—$CH_2$— or —$CH_2$—S—. Perferably X is —$CH_2CH_2$—.

In another preferred embodiment of the invention Y is selected from >N— or >C=C($R^8$)— wherein $R^8$ is hydrogen. Preferably Y is >C=CH—.

In another preferred embodiment of the invention A is the completion of a bond or —($CR^9R^{10}$)— wherein $R^9$ and $R^{10}$ are hydrogen.

In another preferred embodiment of the invention r is 0, 1 or 2.

In another preferred embodiment of the invention s is 0, 1 or 2.

In another preferred embodiment of the invention $R^{12}$ is hydrogen or —$(CH_2)_pCOR^{17}$ wherein p is 0 and wherein $R^{17}$ is —OH or —$NH_2$.

In yet another preferred embodiment of the invention $R^{13}$ is cyano, —$N(CH_3)_2$, —NH—Z or —$(CHR^{21})_q$—Z wherein q is 0 or 1, and wherein $R^{21}$ is hydrogen, cyano or —COOH, and wherein Z is cyclohexyl, phenyl, naphtyl or pyrrolidinyl, which rings may optionally be substituted with halogen or methyl.

Preferred compounds of the present invention include:

1-(3-(10,11-Dihydro-5H-dibenzo[a,d]cyclohepten-5-ylidene)-1-propyl)-4-phenyl-4-piperidinecarboxylic acid;

4-(4-Chlorophenyl)-1-(3-(10,11-dihydro-5H-dibenzo[a,d]cyclohepten-5-ylidene)-1-propyl)-4-piperidinecarboxylic acid;

4-(4-Methylphenyl)-1-(3-(10,11-dihydro-5H-dibenzo[a,d]cyclohepten-5-ylidene)-1-propyl)-4-piperidinecarboxylic acid;

1-(3-(10,11-Dihydro-5H-dibenzo[a,d]cyclohepten-5-ylidene)-1-propyl)-4-anilino-4-piperidinecarboxamide;

2-(1-(3-(10,11-Dihydro-5H-dibenzo[a,d]cyclohepten-5-ylidene)-1-propyl)4-piperidyl)- 2-phenylacetonitrile;

2-(1-(3-(10,11-Dihydro-5H-dibenzo[a,d]cyclohepten-5-ylidene)-1-propyl)-4-piperidinyl)-2-phenylacetic acid;

1-(3-(10,11-Dihydro-5H-dibenzo[a,d]cyclohepten-5-ylidene)-1-propyl)-4-cyano-4 piperidinecarboxylic acid;

1-(3-(10,11-Dihydro-5H-dibenzo[b,f]azepin-5-yl)-1-propyl)-4-phenylpiperidine;

4-Benzyl-1-(3-(10,11-dihydro-5H-dibenzo[a,d]cyclohepten-5-ylidene)-1-propyl)-piperidine;

4-Cyclohexyl-1-(3-(10,11-dihydro-dibenzo[a,d]cyclohepten-5-ylidene)-propyl)-4-piperidinecarboxylic acid;

1-(3-(10,11-Dihydro-dibenzo[a,d]cyclohepten-5-ylidene)-1-propyl)-4-((naphthalen-2-yl)methyl)-4-piperidinecarboxylic acid;

1-(3-(10,11-Dihydro-5H-dibenzo[a,d]cyclohepten-5-ylidene)-1-propyl)-4-pyrrolidino-4-piperidinecarboxylic acid amide;

1-(3-(10,11-Dihydro-dibenzo[a,d]cyclohepten-5-ylidene)-1-propyl)-4-dimethylamino-4-piperidinecarboxamide;

or a pharmaceutically acceptable salt thereof.

It has been demonstrated that the novel compounds of formula I inhibit neurogenic inflammation which involves the release of neuropeptides from peripheral and central endings of sensory C-fibres. Experimentally this can be demonstrated in animal models of histamine induced paw oedema Amann et al. (Europ. J. Pharmacol. 279, 227–231, 1995) in which the novel compounds of formula I exhibit a potent inhibitory effect. Compounds of formula I may be used to treat all painful, hyperalgesic and/or inflammatory conditions in which C-fibres play a pathophysiological role by eliciting neurogenic pain or inflammation, i.e.:

Acutely painful conditions exemplified by migraine, post-operative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, itching, chronic pancreatitis, inflammatory skin disease including psoriasis and autoimmune dermatoses, osteoporotic pain.

Further, it has been demonstrated that the compounds of general formula I lower the glucose levels in diabetic rodents (ob/ob mice and diabetic fat Zucker rats) as well as improve the glucose tolerance and that this may result from the reduced release of CGRP from peripheral nervous endings and other peptides derived from the sensory nervous system. Hence the compounds of general formula I may be used in the treatment of NIDDM as well as ageing-associated obesity. Experimentally this has been demonstrated by the subcutaneous administration of glucose into ob/ob mice with or without previous oral treatment with a compound of general formula I.

The compounds of formula I may be prepared by the following method A:

A compound of formula II wherein $R^1$, $R^2$, $R^{1a}$, $R^{2a}$, X, Y, A, r and s are as defined above and W is a suitable leaving group such as halogen, p-toluene sulphonate or mesylate may be reacted with an azaheterocyclic compound of formula III wherein $R^{12}$ and $R^{13}$ are as defined above to give the compound of formula I. This alkylation reaction may be carried out in a solvent such as acetone, N,N-dimethylformamide, acetonitrile, dibutylether, 2-butanone, ethyl acetate, tetrahydrofuran (THF) or toluene in the presence of a base e.g. sodium hydride, potassium carbonate and a catalyst, e.g. an alkali metal iodide at a temperature up to reflux temperature for the solvent used for e.g. 1 to 120 h. If esters have been prepared in which $R^{17}$ is alkoxy, compounds of formula I wherein $R^{17}$ is OH may be prepared by hydrolysis of the ester group, preferably at room temperature in a mixture of an aqueous alkali metal hydroxide solution and an alcohol such as methanol or ethanol, for example, for about 0.5 to 6 h.

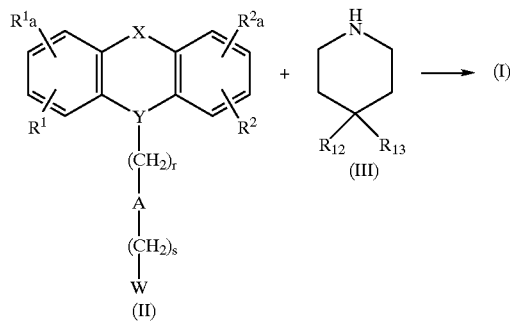

Compounds of formula II and III may readily be prepared by methods familiar to those skilled in the art.

Alternatively, the compounds of formula I may be prepared by the following method B:

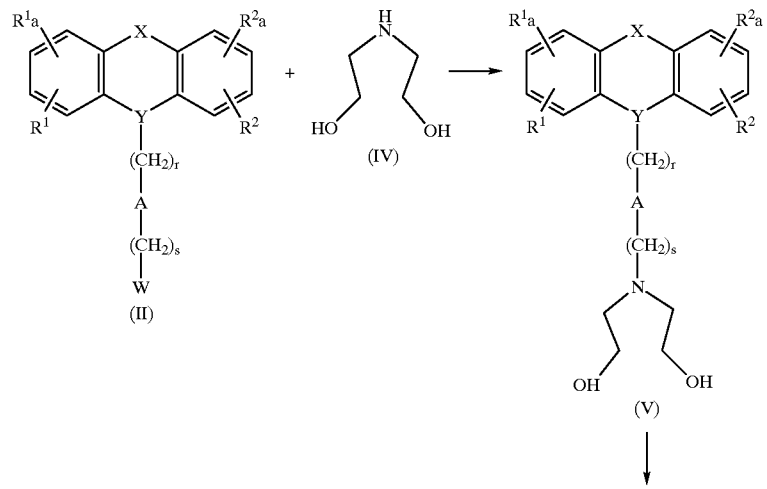

-continued

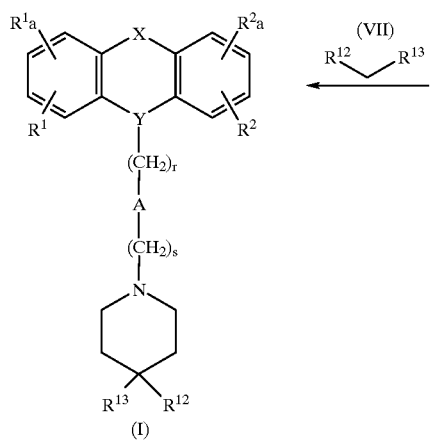

(I)

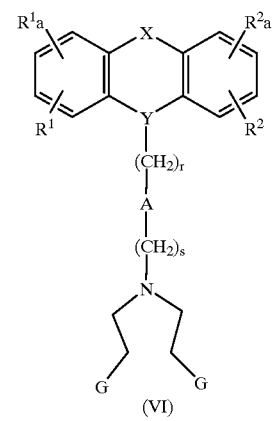

(VI)

A compound of formula II wherein $R^1$, $R^2$, $R^{1a}$, $R^{2a}$, X, Y, A, r and s are as defined above and W is a suitable leaving group such as halogen, p-toluene sulphonate or mesylate may be reacted with an aza compound of formula IV to give a compound of formula V wherein $R^1$, $R^2$, $R^{1a}$, $R^{2a}$, X, Y, A, r and s are as defined above. This alkylation reaction may be carried out in a solvent such as acetone, N,N-dimethylformamide, acetonitrile, dibutylether, 2-butanone, ethyl acetate, tetrahydrofuran (THF) or toluene in the presence of a base e.g. sodium hydride, potassium carbonate and a catalyst, e.g. an alkali metal iodide at a temperature up to reflux temperature for the solvent used for e.g. 1 to 120 h. The compound of formula V may be transformed into a compound of formula VI wherein $R^1$, $R^2$, $R^{1a}$, $R^{2a}$, X, Y, A, r and s are as defined above and G is a suitable leaving group such as halogen, p-toluene sulphonate or mesylate. The compound of formula VI may be reacted with an x-activated compound of formula VII wherein $R^{12}$ and $R^{13}$ are as defined above to give the compound of formula I. This alkylation reaction may be carried out in a solvent such as N,N-dimethylformamide, tetrahydrofuran, ethanol, toluene, N-methylpyrrolidone or hexamethylphosphoramide in the presence of a base e.g. potassium tertbutoxide, sodium ethanolate, sodium hydride, potassium carbonate or triethyl amine at a temperature up to reflux temperature for the solvent used for e.g. 1 to 120 h. If esters have been prepared in which $R^{17}$ is alkoxy, compounds of formula I wherein $R^{17}$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II, IV and VII may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

PHARMACOLOGICAL METHODS

I. Histamine Induced Paw Oedema

The rat histamine paw oedema test was performed essentially as described by Amann et al. (Europ. J. Pharmacol. 279, 227–231, 1995). In brief 250–300 g male Sprague-Dawley rats were anaesthetized with pentobarbital sodium, and placed on a 32 degree Celsius heated table. Ten minutes later histamine (50 micoliter, 3 mg/ml) was injected in the right hind paw and 20 minutes hereafter the paw swelling was determined by water plethysmography (Ugo Basile). Test compounds were administered intraperitoneally at 15 minutes before the anaesthetics.

II. Reduced Release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and tunk blood collected. Immunoreactive CGRP was determined in plasma by radio-immuno-assay. Two groups of animals were used. The one group was vehicle treated, whereas the other group received a compound of formula I via drinking water (100 mg/1) for five days before the test.

Values for inhibition of histamine induced oedema response for some representative compounds are recorded in table 1.

TABLE 1

Inhibition of histamine induced oedema response at 1.0 mg/kg

| Example No. | % Oedema inhibition |
|---|---|
| 1 | 41 |
| 5 | 30 |

PHARMACEUTICAL COMPOSITIONS

The present invention also relates to pharmaceutical compositions comprising, as an active ingredient, at least one of the compounds of the general formula I or a pharmaceutically acceptable salt thereof and, usually, such compositions also contain a pharmaceutically acceptable carrier or diluent.

Pharmaceutical compositions comprising a compound of the present invention may be prepared by conventional techniques, e.g. as described in *Remington: The Science and Practice of Pharmacy*, 19$^{th}$ Ed., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, syrup, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, topical, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| | |
|---|---|
| Core: | |
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as placticizer for film coating.

The compounds of the invention may be administered to a mammal, especially a human in need of such treatment, prevention, elimination, alleviation or amelioration of an indication related to all painful, hyperalgesic and/or inflammatory conditions in which C-fibres play a pathophysiological role such as e.g. neurogenic pain, neurogenic inflammation, migraine, neuropathy, itching and rheumatoid arthritis, as well as indications caused by or related to the secretion and circulation of insulin antagonising peptides, such as non-insulin-dependent diabetes mellitus (NIDDM) or ageing-associated obesity. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, in an effective amount.

The compounds of the invention are effective over a wide dosage range. For example, in the treatment of humans, dosages from about 0.5 to about 1000 mg, preferably from about 1 to about 500 mg of compounds of formula 1, conveniently given from 1 to 5 times daily. A most preferable dosage is from about 50 to about 200 mg per dose when administered to e.g. a human. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 50 to about 200 mg of active ingredient in or together with a pharmaceutically acceptable carrier per unit dosage.

Usually, dosage forms suitable for oral, nasal, pulmonal or transdermal administration comprise from about 0.5 mg to about 1000 mg, preferably from about 1 mg to about 500 mg of the compounds of formula I admixed with a pharmaceutically acceptable carrier or diluent.

The method of treating may be described as the treatment of an indication caused by or related to the secretion and circulation of insulin antagonising peptides like CGRP or amylin in a subject in need thereof, which comprises the step of administering to the said subject a neurologically effective amount of a compound of the invention, or a pharmaceutically acceptable salt thereof.

Any novel feature or combination of features described herein is considered essential to this invention.

EXAMPLES

The process for preparing compounds of formula I and preparations containing them is further illustrated in the following examples, which, however, are not to be construed as limiting.

Hereinafter, TLC is thin layer chromatography, $CDCl_3$ is deuterio chloroform and $DMSO-d_6$ is hexadeuterio dimethylsulfoxide. The structures of the compounds are confirmed by either elemental analysis or NMR, where peaks assigned to characteristic protons in the title compounds are presented where appropriate. $^1H$ NMR shifts ($\delta_H$) are given in parts per million (ppm). M.p. is melting point and is given in °C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

1-(3-(10,11-Dihydro-5H-dibenzo[a,d]cyclohepten-5-ylidene)-1-propyl)-4-phenyl-4-piperidinecarboxylic acid

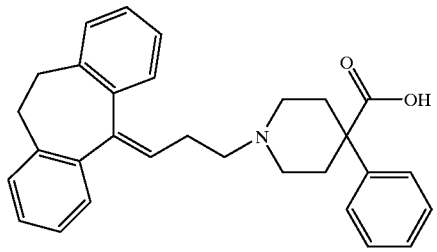

To a solution of 3-(10,11-dihydro-5H-dibenzo[a,d] cyclohepten-5-ylidene)propanol (3.5 g, 14 mmol) in benzene (50 ml), triethylamine (4 ml) and methanesulfonyl chloride (2.0 g, 17.4 mmol) were added and the reaction mixture was stirred at room temperature for 6 h. Water was added and the phases were separated. The organic phase was dried ($MgSO_4$) and solvent was evaporated in vacuo to give a residue which was dissolved in 2-butanone (50 ml). Ethyl 4-phenyl-4-piperidine-carboxylate hydrobromide (4.4 g, 14 mmol) and potassium carbonate (4.4 g, 32 mmol) were added and the mixture was heated at reflux temperature for 24 h. The mixture was filtered and the solvent evaporated in vacuo. The oily residue was purified by column chromatography on silica gel (50 g) using ethyl acetate as eluent to give 5.3 g of 1-(3-(10,11-dihydro-5H-dibenzo[a,d]cyclohepten-5-ylidene)-1-propyl)-4-phenyl-4-piperidinecarboxylic acid ethyl ester as an oil.

TLC: $R_f$=0.25 ($SiO_2$; chloroform/ethanol/ammonium hydroxide=60:2:0.1).

The above ester (4.75 g, 10.5 mmol) was dissolved in ethanol (40 ml) and 5 N sodium hydroxide (5 ml) was added. The mixture was stirred at 40° C. for 20 h, ethanol was evaporated in vacuo and water (50 ml) followed by acetic acid (4 ml) were added. The mixture was extracted with dichloromethane (100 ml), the organic phase was dried ($MgSO_4$) and the solvent was evaporated in vacuo. The residue was crystallised from diethyl ether to give 2.2 g (45%) of the title compound as a solvate with water and acetic acid.

El (m/z):437 ($M^+$, $C_{30}H_{31}NO_2$, 0.1%), 436 (0.1%), 435 (0.1%), 392 (0.1%), 246 (2.6%), 232 (1.5%), 218 (100%), 203 (2.9%), 202 (2.8%), 190 (2.2%), 172 (4.2%), 91 (6%).

Calculated for $C_{29}H_{31}NO_2$, 0.5 $CH_3COOH$, 0.5 $H_2O$: C, 77.56%; H, 7.38%; N, 3.02%; Found: C, 77.50%; H, 6.88%, N, 2.88%.

Example 2

4-(4-Chlorophenyl)-1-(3-(10,11-dihydro-5H-dibenzo [a,d]cyclohepten-5-ylidene)-1-propyl)-4-piperidinecarboxylic acid hydrochloride

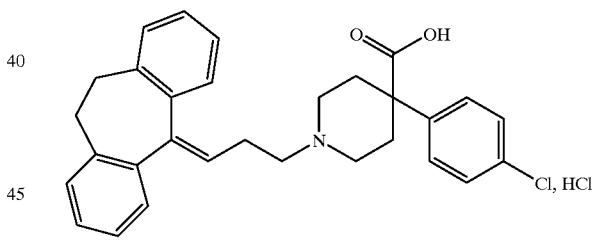

A mixture of ethyl 4-(4-chlorophenyl)-4-piperidincarboxylate toluene-4-sulfonate (2.2 g, 0.005 mol, prepared similarly as described in Pol. Pat. 105 435 or Ber. 74, 1433 (1941) with the exception that the ester was isolated as p-toluenesulfonate), 5-(3-bromo-1-propylidene)-10,11-dihydro-5H-dibenzo[a,d]cycloheptene (2.0 g, 0.0064 mol), anhydrous potassium carbonate (3.00 g, 0.021 mol) and potassium iodide (2.0 g, 0.012 mol) in 2-butanone (60 ml) was stirred at 60–70° C. for 7.5 h. The mixture was diluted with ether (90 ml) and water (60 ml), and the phases were separated. The aqueous phase was extracted with additional ether (60 ml) and the combined organic extracts were washed with water (60 ml) and dried ($MgSO_4$). The solvent was removed in vacuo and the oily residue (3.47 g) was purified by gradient column chromatography on silica gel using mixtures of benzene and ethyl acetate as eluents. The benzene/ethyl acetate (9:1) fraction afforded 2.65 g of 4-(4-chlorophenyl)-1-(3-(10,11-dihydro-5H-dibenzo[a,d] cyclohepten-5-ylidene)-1-propyl)-4-piperidinecarboxylic acid ethyl ester.

TLC: $R_f$=0.65 (SiO$_2$; chloroform saturated with ammonia/ethanol=10:1).

A mixture of the above ester (2.20 g, 0.0044 mol) and 20% sodium hydroxide (2 ml) in ethanol (18 ml) was stirred at room temperature for 24 h and left standing for additional 24 h. Ethanol was evaporated in vacuo and the residue was dissolved in dichloromethane (300 ml). The resulting solution was acidified with acetic acid, washed with water (3×15 ml) and the organic phase was dried (MgSO$_4$). The solvent was evaporated in vacuo, the residue (2.60 g) was dissolved in a mixture of ether and acetone (1:1, 20 ml) and the solution was made acidic with a solution of hydrogen chloride in ether. The solvents were evaporated in vacuo, the amorphous residue was twice dissolved in acetone (20 ml) and re-evaporated in vacuo. The solid was suspended in dry ether (100 ml) and stirred at room temperature for 3 h. The precipitate was filtered off and dried in vacuo, affording 1.85 g (82%) of the title compound.

M.p. 234–239° C.

Calculated for C$_{30}$H$_{30}$ClNO$_2$, HCl, 0.25 H$_2$O: C, 70.24%; H, 6.19%; Cl, 13.82%; N, 2.73%; Found: C, 70.28%; H, 6.22%; Cl, 13.88%; N, 2.60%.

Example 3

4-(4-Methylphenyl)-1-(3-(10,11-dihydro-5H-dibenzo[a,d]cyclohepten-5-ylidene)-1-propyl)-4-piperidinecarboxylic acid hydrochloride

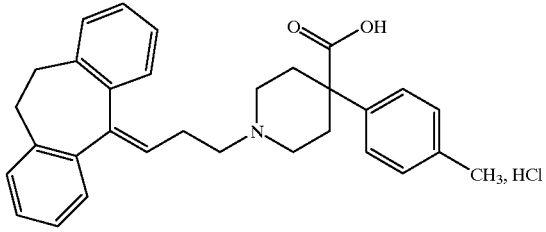

A mixture of ethyl 4-(4-methylphenyl)-4-piperidine carboxylate (3.0 g, 0.012 mol, prepared similarly as described in the method in Pol. Pat. 105 435 or Ber. 74, 1433 (1941)), 5-(3-bromo-1-propylidene)-10,11-dihydro-5H-dibenzo[a,d] cycloheptene (4.50 g, 0.0145 mol), anhydrous potassium carbonate (5.00 g, 0.036 mol) and potassium iodide (4.0 g, 0.024 mol) in 2-butanone (100 ml) was stirred at 80° C. for 7.5 h. The mixture was diluted with ether (150 ml) and water (150 ml) and the layers were separated. The aqueous phase was extracted with additional ether (80 ml) and the combined organic extracts were washed with water (100 ml) and dried (MgSO$_4$). The solvent was removed in vacuo and the oily residue (6.60 g) was purified by gradient column chromatography on silica gel using mixtures of benzene and ethyl acetate as eluents. The benzene/ethyl acetate (9:1) fraction afforded 2.90 g (50%) of 4-(4-methylphenyl)-1-(3-(10,11-dihydro-5H-dibenzo[a,d]cyclohepten-5-ylidene)-1-propyl)-4-piperidinecarboxylic acid ethyl ester.

TLC: $R_f$=0.30 (SiO$_2$; chloroform).

A mixture of the above ester (2.50 g, 0.0052 mol) and 20% sodium hydroxide (3.4 ml) in ethanol (25 ml) was stirred at room temperature for 36 h and left standing for 3 days at room temperature. The ethanol was evaporated in vacuo and the residue was dissolved in di-chloromethane (120 ml). Water (10 ml) was added, the solution was acidified with acetic acid and the aqueous phase was separated. The organic layer was washed with water (10 ml) and dried (MgSO$_4$). The solvent was evaporated in vacuo, the residue (2.30 g) was dissolved in a mixture of ether and acetone (1:1, 20 ml) and the solution was made acidic with a solution of hydrogen chloride in ether. The solvent was decanted from the separated solid, the precipitate was stirred with a new portion of dry ether (20 ml) for 0.5 h and left to stay over-night. After filtration and drying, this afforded 1.8 g (71%) of the title compound.

M.p. 164–170 ° C.

Calculated for C$_{31}$H$_{33}$NO$_2$, HCl, 0.5 H$_2$O: C, 74.91%; H, 7.10%; Cl, 7.13%; N, 2.82%; Found: C, 74.50%; H, 7.21%; Cl, 7.22%; N, 2.65%.

Example 4

1-(3-(10,11-Dihydro-5H-dibenzo[a,d]cyclohepten-5-ylidene)-1-propyl)-4-anilino-4-piperidinecarboxamide dihydrochloride

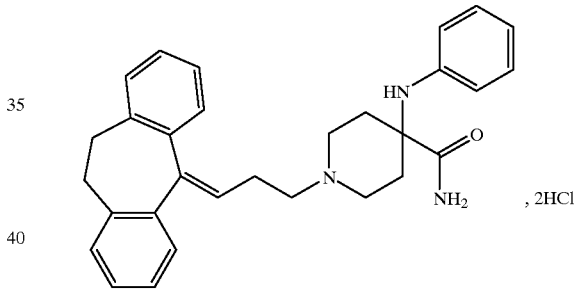

A mixture of 5-(3-bromopropylidene)-10,11-dihydro-5H-dibenzo[a,d]cycloheptene (2.65 g, 8.46 mmol), 4-anilino-4-piperidinecarboxamide (1.85 g, 8.44 mmol, prepared similarly as described in Belg. 777812 (1972)), potassium carbonate (1.3 g, 9.4 mmol) and N,N-dimethylformamide (8 ml) was stirred and heated at 100° C. for 5 h. Benzene (100 ml) and water (100 ml) were added and the phases were separated. The organic phase was dried (K$_2$CO$_3$) and the solvent evaporated in vacuo. The residue was purified by gradient column chromatography on silica gel (30 g) using a mixtures of benzene and ethyl acetate as eluents. This afforded 1.97 g of crude base which was dissolved in diethyl ether and neutralised with hydrogen chloride in diethyl ether. The precipitate was crystallised from a mixture of ethanol and acetone to give 1.70 g (38%) of the title compound as hemihydrate.

M.p. 180–182° C.

Calculated for C$_{30}$H$_{33}$N$_3$O, 2 HCl, 0.5 H$_2$O: C, 67.53%; H, 6.80%; Cl, 13.29%; N, 7.88%; Found: C, 67.67%; H, 6.84%; Cl, 13.37%; N, 7.75%.

Example 5

2-(1-(3-(10,11-Dihydro-5H-dibenzo[a,d]cyclohepten-5-ylidene)-1-propyl)-4-piperidyl)-2-phenylacetonitrile hydrochloride

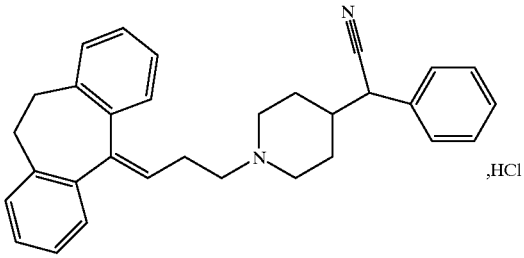

To a solution of 3-(10,11-dihydro-5H-dibenzo[a,d]cyclohepten-5-ylidene)-1-propyl methanesulfonate (4.78 g, 0.0145 mol) in dry N,N-dimethylformamide (20 ml), 2-(4-piperidyl)-2-phenylacetonitrile (4.4 g, 0.0219 mol, prepared similarly as described in Tetrahedron 22, 1996, 272) and potassium carbonate (5.0 g) were added. The reaction mixture was heated at 80° C. for 6 h. After cooling to room temperature, water (120 ml) was added and the mixture was extracted with diethyl ether (2×100 ml). The combined organic extracts were washed with water (3×50 ml). The solvent was evaporated in vacuo and the residue was purified by column chromatography on silica gel (100 g) using chloroform as eluent. This afforded 2.5 g of an oil. The oil was dissolved in diethyl ether (100 ml) and the solution was acidified with hydrogen chloride in diethyl ether. The precipitate was filtered off, washed with diethyl ether and dried in vacuo. This afforded 2.2 g (32%) of the title compound.

M.p. 125–131° C.

Calculated for $C_{31}H_{32}N_2$, HCl, 0.5 $H_2O$: C, 77.88%; H, 7.17%; N, 5.86%; Cl, 7.42%. Found: C, 77.95%; H, 7.05%; N, 6.05%; Cl, 7.54%.

Example 6

2-(1-(3-(10,11-Dihydro-5H-dibenzo[a,d]cyclohepten-5-ylidene)-1-propyl)-4-piperidinyl)-2-phenylacetic acid hydrochloride

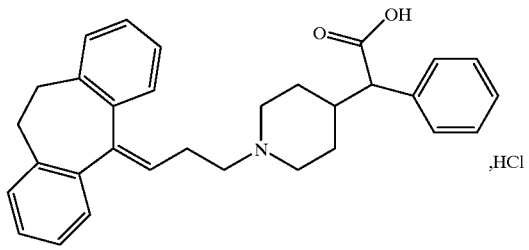

To a solution of 3-(10,11-dihydro-5H-dibenzo[a,d]cyclohepten-5-ylidene)-1-propyl methane-sulphonate (5.4 g, 0.0165 mol) in 2-butanone (80 ml), α-phenyl-α-(4-piperidyl)acetic acid ethyl ester (4.0 g, 0.0165 mol, prepared similarly as described in Brit. pat. 589625, C.A. 42, 226 (1948)) and potassium carbonate (5.7 g, 0.0412 mol) were added and the reaction mixture was heated for 4 h at 50° C., left overnight at room temperature and heated at reflux temperature for 8 h. The precipitated solid was filtered off and the filtrate was evaporated in vacuo. The residue (8.88 g) was purified by column chromatography on silica gel (300 g) using chloroform as eluent. This afforded 4.4 g (56%) of 2-(1-(3-(10,11-dihydro-5H-dibenzo[a,d]-cyclohepten-5-ylidene)-1-propyl)-4-piperidinyl)-2-phenylacetic acid ethyl ester as an oil.

TLC: $R_f$=0.20 ($SiO_2$; chloroform).

To a solution of the above ester (2.0 g, 0,00416 mol) in ethanol (18.5 ml), a solution of sodium hydroxide (0.62 g) in water (2.4 ml) was added. The reaction mixture was stirred at room temperature for 3 days and then heated at reflux temperature for 8 h. Concentrated hydrochloric acid (2.4 ml) and dichloromethane (120 ml) were added, the organic layer was separated, dried ($MgSO_4$) and evaporated in vacuo. The residue was stirred with acetone (40 ml), and the solid was filtered off and washed with acetone. This afforded 1.1 g (54%) of the title compound.

M.p. 240–255° C. (decomp.)

Calculated for $C_{31}H_{33}NO_2$, HCl, 0.5 $H_2O$: C, 74.90%; H, 7.10%; N, 2.81%; Cl, 7.13%; Found: C, 74.96%; H, 7.36%; N, 2.81%; Cl, 7.10%.

Example 7

1-(3-(10,11-Dihydro-5H-dibenzo[a,d]cyclohepten-5-ylidene)-1-propyl)-4-cyano-4 piperidinecarboxylic acid

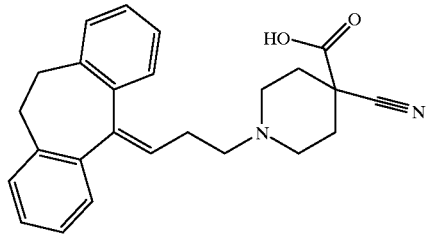

Methanesulfonic acid 3-(10,11-dihydro-5H-dibenzo[a,d]cyclohepten-5-ylidene)-1-propyl ester (13.0 g, 39 mmol) and diethanolamine (5.2 g, 50 mmol) was suspended in acetonitrile (100 ml) and heated at 50° C. for 20 h. The reaction mixture was cooled to room temperature, water (300 ml) was added and the mixture was extracted with ether (3×60 ml). The combined organic phases were washed with brine (50 ml), dried ($MgSO_4$) and concentrated in vacuo. The oily residue was purified by column chromatography on silica gel (130 g) using tetrahydrofuran as eluent. This furnished 10.2 g (75%) of bis(2-hydroxyethyl)-(3-(10,11-dihydro-5H-dibenzo[a,d]cyclohepten-5-ylidene)-1-propyl)-amine as a sticky oil.

To the above diethanol amine (10. g, 29 mmol) dissolved in dichloromethane (200 ml) thionyl chloride (10.7 g, 90 mmol) was added at 0° C. and the mixture was left standing at room temperature for 6 h. The crude reaction mixture was concentrated in vacuo, stripped with tetrahydrofuran (100 ml), re-dissolved in dichloromethane (50 ml) and precipitated with petroleumether (100 ml). After 30 minutes the solvent was decanted of, and the sticky residue was left in vacuo overnight. This afforded 8.9 g (75%) of bis(2-chloroethyl)-(3-(10,11-dihydro-5H-dibenzo[a,d]cyclohepten-5-ylidene)-1-propyl)-amine hydrochloride.

The above chloride (0.50 g, 1.2 mmol), ethyl cyanoacetate (0.45 g, 4 mmol), (0.55 g, 4 mmol) were suspended in N,N-dimethylformamide (10 ml). Potassium tert-butoxide (0.25 g, 2 mmol) was added and the reaction mixture was left at room temperature overnight. Ice water (50 ml) was added and the reaction mixture was extracted with ether (3×50 ml). The combined organic phases were dried (MgSO$_4$) and concentrated in vacuo . The resulting oil was purified by column chromatography on silica gel (20 g) using a mixture of dichloromethane and methanol (20:1) as eluent. The pure fractions were combined, concentrated in vacuo and dissolved in ethanol (10 ml). Sodium hydroxide (0.40 g, 10 mol) was added and the mixture was stirred for 30 minutes. Water (20 ml) was added and the mixture was extracted with ether (20 ml). The aqueous phase was adjusted to pH 2 with 1 N hydrochloric acid and extracted with dichloromethane (3×50 ml). The combined organic phases were dried (MgSO$_4$) and concentrated in vacuo. The crude product was recrystallised from deuterochloroform affording the title compound 0.09 g (17%) as a powder.

TLC: R$_f$=0.55 (SiO$_2$: dichloromethane/methanol/acetic acid=10:2:1).

HPLC retention time=21.32 minutes (5 mm C18 4×250 mm column, eluting with a 20–80% gradient of 0.1% trifluoroacetic acid/acetonitrile and 0.1% trifluoroacetic acid/water over 30 minutes at room temperature).

Example 8

1-(3-(10,11-Dihydro-5H-dibenz[b,f]azepin-5-yl)-1-propyl)-4-phenylpiperidine hydrogen oxalate

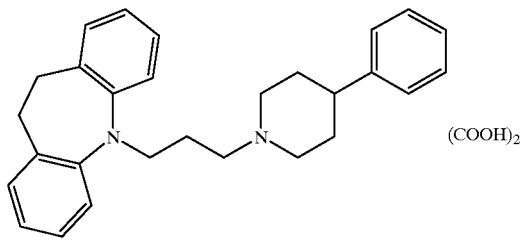

A mixture of 3-(10,11-dihydro-5H-dibenz[b,f]azepin-5-yl)-propyl methanesulfonate (2.6 g, 7.85 mmol), 4-phenylpiperidine (1.6 g, 9.94 mmol), potassium carbonate (3.0 g, 21.7 mmol) and methyl ethyl ketone (50 ml) was heated and stirred at 80° C. for 24 h. The mixture was filtered and the solvent was removed by evaporation in vacuo. The crude residue was purified by column chromatography on silica gel (35 g) using ethyl acetate as eluent. This afforded 2.4 g (77%) of 1-(3-(10,11-dihydro-5H-dibenzo[b,f]azepin-5-yl)-1-propyl)-4-phenylpiperidine as an oily base. The corresponding hydrogen oxalate was prepared by treatment with oxalic acid in a mixture of acetone and diethyl ether.

M.p. 157–159° C.

Calculated for C$_{28}$H$_{32}$N$_2$, C$_2$H$_2$O$_4$: C, 74.05%; H, 7.04%; N, 5.76% Found: C, 73.87%; H, 7.14%; N, 5.81%.

Example 9

4-Benzyl-1-(3-(10,11-dihydro-5H-dibenzo[a,d]cyclohepten-5-ylidene)-1-propyl)-piperidine hydrochloride

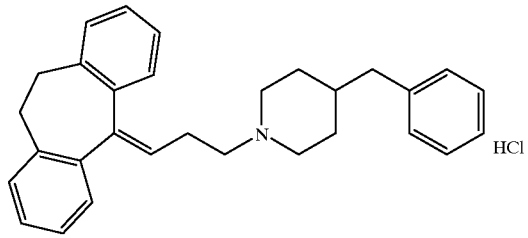

A mixture of 5-(3-bromo-1-propylidene)-10,11-dihydro-5H-dibenzo[a,d]cycloheptene (1.56 g, 0.005 mol), 4-benzylpiperidine (1.75 g, 0.01 mol) and anhydrous potassium carbonate (2.8 g) in N,N-dimethylformamide (50 ml) was heated at 100° C. for 2 h. After cooling, the reaction mixture was diluted with benzene (100 ml), washed with water (5×50 ml), dried (K$_2$CO$_3$) and evaporated in vacuo. The oily residue (2.8 g) was purified by chromatography on silica gel (80 g) using chloroform as eluent. This afforded 1.95 g of 4-benzyl-1-(3-(10,11-dihydro-5H-dibenzo[a,d]cyclohepten-5-ylidene)-1-propyl)-piperidine as an oil, which was dissolved in diethyl ether and treated with a solution of hydrogen chloride in diethyl ether. The precipitate was filtered off, washed with diethyl ether and dried in vacuo to yield 1.92 g (87%) of the title compound.

M.p. 134–136° C.

Calculated for C$_{30}$H$_{32}$N, HCl, 0.25 H$_2$O: C, 80.51%; H, 7.54%; Cl, 7.92%; N, 3.13%; Found: C, 80.43%; H, 7.73%; Cl, 8.26%; N, 3.36%.

Example 10

4-Cyclohexyl-1-(3-(10,11-dihydro-dibenzo[a,d]cyclohepten-5-ylidene)-propyl)-4-piperidinecarboxylic acid hydrochloride

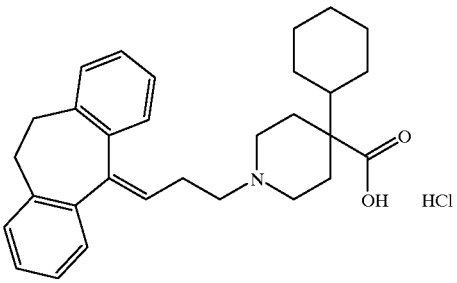

A mixture of 5-(3-bromopropylidene)-5H-dibenzo[a,d]cycloheptene (4.45 g, 14.2 mmol), ethyl 4-cyclohexyl-4-piperidinecarboxylate (3.4 g, 14.2 mmol, prepared similarly as described in Brit. 1 124 661 (1967)), potassium carbonate (2.1 g, 15.2 mmol) and N,N-dimethylformamide (10 ml) was heated at 120° C. for 5 h. Benzene (50 ml) and water (50 ml) were added and the phases were separated. The organic phase was dried and the solvent evaporated in vacuo. The residue was purified by chromatography on silica gel (50 g) using mixtures of benzene and chloroform as eluents to give 2.6 g (39%) of 1-(3-(5H-dibenzo[a,d]cyclohepten-5-ylidene)-1-propyl)-4-cyclohexyl4-piperidinecarboxylic acid ethyl ester as an oil.

TLC: $R_f$=0.65 (SiO$_2$: chloroform/ethanol/ammonia= 30:1:0.05).

The above ester (1.2 g, 2.5 mmol) was dissolved in tert-butanol (30 ml) and potassium hydroxide (10 g) was added. The mixture was heated at 120° C. for 10 h. Water (50 ml) followed by benzene (50 ml) were added and the phases were separated. The aqueous phase was treated with acetic acid and extracted with dichloromethane. The combined organic phases were dried (MgSO$_4$) and the solvent evaporated in vacuo. The residue was dissolved in dichloromethane, treated with hydrogen chloride in diethyl ether and the solvents were evaporated in vacuo. The residue was triturated with diethyl ether. This afforded 0.68 g (55%) of the title compound.

M.p.241–246° C.

Calculated for $C_{30}H_{38}NO_2$, HCl, H$_2$O: C, 72.34%; H, 8.09%; N, 2.81%; Cl, 7.12%, Found: C, 72.09%; H, 8.06%; N, 2.56%; Cl, 6.92%.

Example 11

1-(3-(10,11-Dihydro-dibenzo[a,d]cyclohepten-5-ylidene)-1-propyl)-4-((naphthalen-2-yl)methyl)-4-piperidinecarboxylic acid hydrochloride

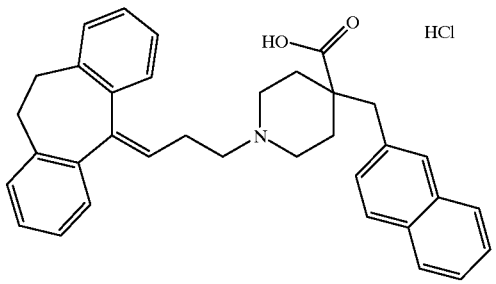

To potassium hexamethyldisilazane (31.5 mmol, prepared from hexamethyldisilazane (5.3 g, 32.8 mmol) and potassium hydride (6.3 g, 31.5 mmol, 20% suspension in oil)) ) in tetrahydrofuran (40 ml) ethyl 1-tert-butyloxycarbonyl-4-piperidinecarboxylate (7.0 g, 26.9 mmol) in tetrahydrofuran (50 ml) was added drop wise at –70° C. under stirring. After 30 minutes 2-naphtylmethylbromide (5.6 g, 25.3 mmol) in tetrahydrofuran (30 ml) was added. Stirring was continued at –70° C. for 2 h and the mixture was then allowed to stand overnight. Water (30 ml) was added and the mixture was extracted with ethyl acetate (200 ml), the organic phase was dried (MgSO$_4$) and the solvent was evaporated in vacuo. The residue was purified by chromatography on silica gel (100 g) using benzene and chloroform as eluents to give ethyl 1-tert-butyloxycarbonyl-4-(2-naphtylmethyl)-4-piperidinecarboxylate (4.8 g) as an oil.

TLC: $R_f$=0.60 (SiO$_2$: benzene/diethyl ether=1:1).

The above ester was dissolved in ethyl acetate and the solution was treated with gaseous hydrogen chloride at 0° C. for 2 h. After standing overnight the solvent was evaporated in vacuo and the residue was treated with ammonium hydroxide and extracted with diethyl ether. The organic phase was dried (K$_2$CO$_3$) and the solvent was evaporated affording ethyl 4-(2-naphtylmethyl)-4-piperidinecarboxylate (3.2 g).

TLC: $R_f$=0.20 (SiO$_2$: benzene/diethyl ether=1:1).

The above ester (3.2 g, 10.7 mmol) was dissolved in N,N-dimethylformamide (10 ml), 5-(3-bromopropylidene)-5H-dibenzo[a,d]cycloheptene (3.4 g, 10.8 mmol) and potassium carbonate (1.6 g, 11.6 mmol) were added. The mixture was heated at 100° C. for 7 h. Benzene (50 ml) and water (50 ml) were added and the phases were separated. The organic phase was dried and the solvent evaporated in vacuo. The residue was purified by chromatography on silica gel (50 g) using mixtures of benzene and chloroform as eluents to give 44.0 g (71%) of 1-(3-(5H-dibenzo[a,d]cyclohepten-5-ylidene)-1-propyl)-4-(2-naphtylmethyl)-4-piperidinecarboxylic acid ethyl ester as an oil.

TLC: $R_f$=0.75 (SiO$_2$: chloroform/ethanol/ammonium hydroxide=20:1:0.05)

The above ester (2.28 g, 4.3 mmol) was dissolved in tert-butanol (30 ml) and potassium hydroxide (10 g) was added. The mixture was heated at 120° C. for 10 h. Water (50 ml) followed by benzene (50 ml) were added and the phases were separated. The organic phase was dried and the solvent was evaporated in vacuo. The residue was dissolved in acetone, treated with hydrogen chloride in diethyl ether, filtered (Norite) and evaporated. The residue was triturated with diethyl ether, affording 1.35 g (61%) of the title compound as an amorphous solid.

Calculated for $C_{35}H_{35}NO_2$, HCl, 0.5 H$_2$O: C, 76.83%; H, 6.82%; N, 2.56%; Cl, 6.48%, Found: C, 76.91%; H, 7.17%; N, 2.34%; Cl, 6.30%

Example 12

1-(3-(10,11-Dihydro-5H-dibenzo[a,d]cyclohepten-5-ylidene)-1-propyl)-4-pyrrolidino-4-piperidinecarboxylic acid amide dihydrochloride

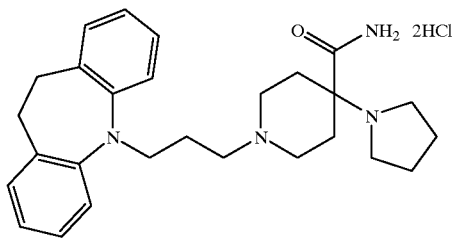

To a solution of 1-benzyl-4-pyrrollidino-4-piperidinecarboxylic acid amide (4.18 g, 0.0145 mol) in methanol (110 ml), Pd(OH)$_2$/C catalyst (1.1 g) was added and the reaction mixture was hydrogenated at 1.6 to 1.3 MPa at room temperature. The catalyst was filtered off and the filtrate evaporated in vacuo. This afforded 2.8 g (100%) of 4-pyrrolidino-4-piperidinecarboxylic acid amide as a solid.

A mixture of the above piperidine (2.43 g, 0.0123 mol), 3-(10,11-dihydro-5H-dibenzo[b,f]azepin-5-yl)propyl methanesulfonate (4.05 g, 0.129 mol), potassium carbonate (3.4 g, 0.0246 mol) and sodium iodide (0.2 g) in N,N-dimethylformamide (80 ml) was stirred at 60° C. for 5 h and left overnight at room temperature. The reaction mixture was diluted with benzene (200 ml), the solid was filtered off and the filtrate was washed with water (4×100 ml), dried (MgSO$_4$) and evaporated in vacuo. The residue (2.86 g) was purified by gradient column chromatography on silica gel (400 g) using chloroform and a mixture of chloroform saturated with ammonia and MeOH (100:1) as eluents. This afforded 2.30 g (44%) of 1-(3-(10,11-dihydro-5H-dibenzo[a,d]cyclohepten-5-ylidene)-1-propyl)-4-pyrrolidine-4-piperidinecarboxylic acid amide as an oil.

TLC: R$_f$=0.18 (SiO$_2$: methanol/chloroform saturated with ammonia=1:9).

The above carboxylic acid amide (2.30 g) was dissolved in ethanol (15 ml) and the solution was treated with ether saturated with hydrogen chloride. The mixture was stirred for 2 h and the precipitate was filtered off, washed with ether (3×30 ml) and dried. This afforded 2.6 g of the title compound.

M.p. 219–224° C.

Calculated for C$_{27}$H$_{36}$N$_4$O, 2 HCl, H$_2$O: C, 61.94%; H, 7.70%; N, 10.70%; Cl, 13.54%; Found: C, 62.03%; H, 7.48%; N, 10.55%; Cl, 13.74%.

Example 13

1-(3-(10,11-Dihydro-dibenzo[a,d]cyclohepten-5-ylidene)-1-propyl)-4-dimethylamino-4-piperidinecarboxamide dihydrochloride

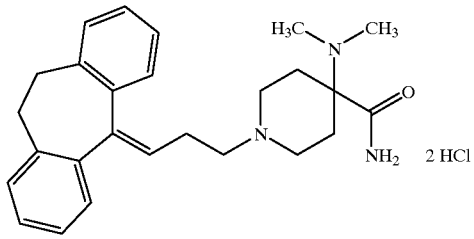

A mixture of 5-(3-bromopropylidene)-10,11-dihydro-5H-dibenzo[a,d]cycloheptene (1,87 g, 6.0 mmol), 4-dimethylamino-4-piperidinecarboxamide dihydrochloride (1,5 g, 6.2 mmol, described in J.Med.Chem. 7, 619 (1964)), potassium carbonate (4.1 g, 30 mmol), potassium iodide (1.0 g, 6.0 mmol) and 2-butanone (30 ml) was stirred at reflux temperature for 10 h. The mixture was filtered and the solvent was evaporated, affording 2.8 g of an oil. This was purified by chromatography on silica gel (150 g) using chloroform and mixtures of chloroform and 5, 10, 20, 30 or 40% of ethanol as eluents to give 1.4 g (58%) of 1-(3-(10,11-dihydro- 5H-dibenzo[a,d]cyclohepten-5-ylidene)-1-propyl)-4-dimethylamino-4-piperidinecarboxamide as a solid. The solid was dissolved in acetone (15 ml) and treated with concentrated hydrochloric acid (0.7 ml). The resulting mixture was stirred for 2 h at room temperature and then filtered. The solid was washed with acetone (5 ml) and dried, affording 1.3 g of the title compound.

M.p. 245–248° C.

Calculated for C$_{26}$H$_{33}$N$_3$O, 2 HCl, 0.25 H$_2$O: C, 64.92%; H, 7.44%; N, 8.74%; Cl, 14.74%; Found: C, 64.95%; H, 7.36%; N, 8.66%; Cl, 14.59%.

What is claimed is:
1. A compound of formula I

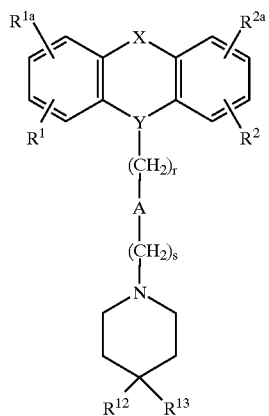

wherein R$^1$, R$^{1a}$, R$^2$ and R$^{2a}$ independently are hydrogen, halogen, cyano, trifluoromethyl, methylthio, hydroxy, C$_{1-6}$-alkyl or C$_{1-6}$-alkoxy;

X is ortho-phenylene, —CH$_2$CH$_2$—, —CH=CH—CH$_2$—, —CH$_2$—CH=CH—, —CH$_2$—(C=O)—, —(C=O)—CH$_2$—, —CH$_2$CH$_2$CH$_2$—, —CH=CH—, —N(R$^5$)—(C=O)—, —(C=O)—N(R$^5$)—, —O—CH$_2$—O—, —CH$_2$—O—CH$_2$—, —(CH$_2$)N(R$^5$)—, —N(R$^5$)(CH$_2$)—, —N(CH$_3$)SO$_2$—, —SO$_2$N(CH$_3$)—, —CH(R$^6$)CH$_2$—, —CH$_2$CH(R$^6$)—, —(C=O)— or —N(R$^7$)— wherein R$^5$ and R$^7$ independently are hydrogen or C$_{1-6}$-alkyl and wherein R$^6$ is C$_{1-6}$-alkyl or phenyl;

Y is >N—, >CH—, >N—(C=O)— or >C=C(R$^8$)— wherein only the underscored atom participates in the ring system and wherein R$^8$ is hydrogen or C$_{1-6}$-alkyl;

A is —CH=CR$^9$—, —CR$^9$=CH—, —C=C—, —(C=O)—, —(C=CH$_2$)—, —(CR$^9$R$^{10}$)—, —CH(OR$^{11}$)—, —CH(NHR$^{11}$)—, phenylene, C$_{3-7}$-cycloalkylene or the completion of a bond wherein R$^9$ and R$^{10}$ independently are hydrogen, C$_{1-6}$-unbranched alkyl, C$_{3-6}$-branched alkyl or C$_{3-8}$-cycloalkyl and wherein R$^{11}$ is hydrogen or C$_{1-6}$-alkyl;

r and s independently are 0, 1, 2, 3 or 4;

R$^{12}$ is hydrogen, —(CH$_2$)$_N$OH or —(CH$_2$)$_p$COR$^{17}$ wherein n is 1, 2, 3, 4, 5 or 6 and wherein p is 0 or 1 and wherein R$^{17}$ is —OH, —NHR$^{20}$ or C$_{1-6}$-alkoxy wherein R$^{20}$ is hydrogen or C$_{1-6}$-alkyl; and R$^{13}$ is cyano, —NR$^5$—Z or —(CHR$^{21}$)$_q$—Z wherein R$^5$ is as defined above and wherein q is 0, 1, 2, 3, 4, 5 or 6, and wherein R$^{21}$ is hydrogen, halogen, cyano, trifluoromethyl, hydroxy, C$_{1-6}$-alkyl, C$_{1-6}$-alkoxy, —NR$^5$R$^7$ or —COOH, and wherein Z is C$_{3-8}$-cycloalkyl, phenyl, naphthyl or pyrrolidinyl, which rings may optionally be substituted with one or more of halogen, cyano, trifluoromethyl, hydroxy, methylthio, C$_{1-6}$-alkyl or C$_{1-6}$-alkoxy; or a pharmaceutically acceptable salt thereof.

2. A compound according to claim 1 wherein R$^1$, R$^{1a}$, R$^2$ and R$^{2a}$ independently are hydrogen, halogen, trifluoromethyl or C$_{1-6}$-alkyl.

3. A compound according to claim 1 wherein X is —CH$_2$CH$_2$—, —CH=CH— or —OCH$_2$O—.

4. A compound according to claim 1 wherein Y is >N— or >C=CH—.

5. A compound according to claim 1 wherein A is the completion of a bond or —($CR^9R^{10}$)— wherein $R^9$ and $R^{10}$ are hydrogen.

6. A compound according to claim 1 wherein r is 0, 1 or 2.

7. A compound according to claim 1 wherein s is 0, 1 or 2.

8. A compound according to claim 1 wherein $R^{12}$ is hydrogen or —$(CH_2)_pCOR^{17}$ wherein p is 0 and wherein $R^{17}$ is —OH or —$NH_2$.

9. A compound according to claim 1 wherein $R^{13}$ is cyano, —NH—Z or —$(CHR^{21})_q$—Z wherein q is 0 or 1, and wherein $R^{21}$ is hydrogen, cyano or —COOH, and wherein Z is cyclohexyl, phenyl, naphthyl or pyrrolidinyl, which rings may optionally be substituted with halogen or methyl.

10. A compound according to claim 1 selected from the following:

1-(3-(10,11-Dihydro-5H-dibenzo[a,d]cyclohepten-5-ylidene)-1-propyl)-4-phenyl-4-piperidinecarboxylic acid;

4-(4-Chlorophenyl)-1-(3-(10,11-dihydro-5H-dibenzo[a,d]cyclohepten-5-ylidene)-1-propyl)-4-piperidinecarboxylic acid;

4-(4-Methylphenyl)-1-(3-(10,11-dihydro-5H-dibenzo[a,d]cyclohepten-5-ylidene)-1-propyl)-4-piperidinecarboxylic acid;

1-(3-(10,11-Dihydro-5H-dibenzo[a,d]cyclohepten-5-ylidene)-1-propyl)-4-anilino-4-piperidinecarboxamide;

2-(1-(3-(10,11-Dihydro-5H-dibenzo[a,d]cyclohepten-5-ylidene)-1-propyl)-4-piperidyl)- 2-phenylacetonitrile;

2-(1-(3-(10,11-Dihydro-5H-dibenzo[a,d]cyclohepten-5-ylidene)-1-propyl)-4-piperidinyl)-2-phenylacetic acid;

1-(3-(10,11-Dihydro-5H-dibenzo[a,d]cyclohepten-5-ylidene)-1-propyl)-4-cyano-4 piperidinecarboxylic acid;

1-(3-(10,11-Dihydro-5H-dibenzo[b,f]azepin-5-yl)-1-propyl)-4-phenylpiperidine;

4-Benzyl-1-(3-(10,11-dihydro-5H-dibenzo[a,d]cyclohepten-5-ylidene)-1-propyl)-piperidine;

4-Cyclohexyl-1-(3-(10,11-dihydro-dibenzo[a,d]cyclohepten-5-ylidene)-propyl)-4-piperidinecarboxylic acid;

1-(3-(10,11-Dihydro-dibenzo[a,d]cyclohepten-5-ylidene)-1-propyl)-4-((naphthalen-2-yl)methyl)-4-piperidinecarboxylic acid;

1-(3-(10,11-Dihydro-5H-dibenzo[a,d]cyclohepten-5-ylidene)-1-propyl)-4-pyrrolidino-4-piperidinecarboxylic acid amide;

or a pharmaceutically acceptable salt thereof.

11. A compound which is 1-(3-(10,11-Dihydro-dibenzo[a,d]cyclohepten-5-ylidene)-1-propyl)-4-dimethylamino-4-piperidinecarboxamide;

or a pharmaceutically acceptable salt thereof.

12. A pharmaceutical composition comprising as an active component an effective amount of a compound according to claim 1 together with a pharmaceutically acceptable carrier or diluent.

13. The pharmaceutical composition according to 12 comprising between 0.5 mg and is 1000 mg of the compound per unit dose.

14. A method of treating neurogenic inflammation comprising administering to a subject in need thereof an effective amount of a compound according to claim 1.

15. A method of treating neuropathy comprising administering to a subject in need thereof an effective amount of a compound according to claim 1.

16. A method of treating rheumatoid arthritis comprising administering to a subject in need thereof an effective amount of a compound according to claim 1.

17. A method of treating non-insulin-dependent diabetes mellitus (NIDDM) comprising administering to a subject in need thereof an effective amount of a compound according to claim 1.

18. A method of treating non-insulin-dependent diabetes mellitus (NIDDM) comprising administering to a subject in need thereof a pharmaceutical composition according to claim 12.

\* \* \* \* \*